(12) United States Patent
    Gregory

(10) Patent No.: US 11,590,276 B2
(45) Date of Patent: Feb. 28, 2023

(54) RECTAL DRAIN APPLIANCE

(71) Applicant: ConvaTec Technologies Inc., Las Vegas, NV (US)

(72) Inventor: Christopher Gregory, Bridgewater, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 668 days.

(21) Appl. No.: 16/565,406

(22) Filed: Sep. 9, 2019

(65) Prior Publication Data

US 2020/0030521 A1    Jan. 30, 2020

Related U.S. Application Data

(60) Division of application No. 15/224,278, filed on Jul. 29, 2016, now Pat. No. 10,406,277, which is a
(Continued)

(51) Int. Cl.
    *A61M 3/02*      (2006.01)
    *A61M 25/10*     (2013.01)
    (Continued)

(52) U.S. Cl.
    CPC ............ *A61M 3/0295* (2013.01); *A61M 1/85* (2021.05); *A61M 25/1018* (2013.01);
    (Continued)

(58) Field of Classification Search
    CPC ............ A61M 1/85; A61M 2210/1064; A61M 2210/1067; A61M 25/04; A61M 25/1018;
    (Continued)

(56) References Cited

U.S. PATENT DOCUMENTS 3,625,199 A * 12/1971 Summers ................. A61B 5/03
                                                     600/561
4,356,610 A * 11/1982 Hon ...................... A61M 25/00
                                                     141/98
(Continued)

FOREIGN PATENT DOCUMENTS

EP    3001976 A1    4/2016
EP    3100758 A1    12/2016
(Continued)

*Primary Examiner* — Adam Marcetich
(74) *Attorney, Agent, or Firm* — Taft Stettinius & Hollister LLP

(57) ABSTRACT

A rectal drainage appliance is disclosed comprising a tubular element having an inflatable balloon at a distal end for anchoring the appliance in the rectum. The appliance includes one or more of: (i) first and second auxiliary lumens communicating with the inflatable balloon to provide independent inflation and pressure monitoring paths coupled to the balloon; (ii) a pressure state indicator defined by a mechanical element configured to flip between first and second states or shapes responsive to sensed pressure; and (iii) a collapsible auxiliary lumen larger than the inflation lumen, and configured to permit admission of irrigation fluid. The pressure state indicator may also be used in intestinal drains.

20 Claims, 5 Drawing Sheets

Related U.S. Application Data continuation of application No. 12/990,229, filed as application No. PCT/US2009/042544 on May 1, 2009, now Pat. No. 9,943,640.

(60) Provisional application No. 61/049,578, filed on May 1, 2008.

(51) Int. Cl.
  *A61M 1/00* (2006.01)
  *A61M 25/04* (2006.01)

(52) U.S. Cl.
  CPC .......... *A61M 25/10184* (2013.11); *A61M 25/10185* (2013.11); *A61M 25/10187* (2013.11); *A61M 25/04* (2013.01); *A61M 2210/1064* (2013.01); *A61M 2210/1067* (2013.01)

(58) Field of Classification Search
  CPC ...... A61M 25/10184; A61M 25/10185; A61M 25/10187; A61M 3/0295; A61M 2025/0025; A61M 2025/0003; A61B 17/3439
  See application file for complete search history.

(56) References Cited

U.S. PATENT DOCUMENTS

| | | | | |
|---|---|---|---|---|
| 4,406,656 A | * | 9/1983 | Hattier | A61M 25/0009 604/523 |
| 4,601,713 A | * | 7/1986 | Fuqua | A61M 25/0032 604/528 |
| 5,108,364 A | * | 4/1992 | Takezawa | A61M 1/85 600/561 |
| 5,464,398 A | * | 11/1995 | Haindl | A61M 25/0026 604/523 |
| 5,503,616 A | * | 4/1996 | Jones | A61B 1/00135 600/156 |
| 5,807,311 A | * | 9/1998 | Palestrant | A61M 25/003 604/537 |
| 5,868,717 A | * | 2/1999 | Prosl | A61M 25/0023 604/6.01 |
| 6,096,013 A | * | 8/2000 | Hakky | A61M 25/04 604/349 |
| 6,270,477 B1 | * | 8/2001 | Bagaoisan | B29C 55/04 606/192 |
| 6,530,898 B1 | * | 3/2003 | Nimkar | A61M 16/044 604/100.01 |
| 6,705,320 B1 | * | 3/2004 | Anderson | A61M 16/04 128/207.14 |
| 10,207,076 B2 | | 2/2019 | Foley et al. | |
| 10,426,584 B2 | | 10/2019 | McClurg | |
| 10,426,654 B2 | | 10/2019 | Ugarte | |
| 10,426,918 B2 | | 10/2019 | Foley et al. | |
| 10,426,919 B2 | | 10/2019 | Erbey, II et al. | |
| 10,434,282 B2 | | 10/2019 | Kearns et al. | |
| 10,441,454 B2 | | 10/2019 | Tanghoej et al. | |
| 10,449,083 B2 | | 10/2019 | Pierson | |
| 10,449,327 B2 | | 10/2019 | Overtoom | |
| 10,449,328 B2 | | 10/2019 | Tanghoej et al. | |
| 10,449,329 B2 | | 10/2019 | Foley et al. | |
| 10,463,466 B2 | | 11/2019 | Cullison | |
| 10,463,833 B2 | | 11/2019 | Clarke et al. | |
| 10,470,861 B2 | | 11/2019 | Khamis et al. | |
| 10,485,483 B1 | | 11/2019 | Brody | |
| 10,485,644 B2 | | 11/2019 | Orr et al. | |
| 10,493,230 B2 | | 12/2019 | Guldager et al. | |
| 10,493,231 B2 | | 12/2019 | McMenamin et al. | |
| 10,493,252 B2 | | 12/2019 | Browne et al. | |
| 10,506,965 B2 | | 12/2019 | Cooper et al. | |
| 10,512,713 B2 | | 12/2019 | Erbey, II et al. | |
| 10,531,894 B2 | | 1/2020 | Connors et al. | |
| 10,531,976 B2 | | 1/2020 | Palmer | |
| 10,548,523 B2 | | 2/2020 | Ahmadi et al. | |
| 10,569,046 B2 | | 2/2020 | Steindahl et al. | |
| 10,569,047 B2 | | 2/2020 | Farrell et al. | |
| 10,569,051 B2 | | 2/2020 | Conway et al. | |
| 10,575,935 B2 | | 3/2020 | Wei et al. | |
| 10,588,774 B2 | | 3/2020 | Alhaqqan | |
| 10,589,061 B2 | | 3/2020 | Palmer | |
| 10,589,093 B2 | | 3/2020 | Imran | |
| 10,610,344 B2 | | 4/2020 | Shapiro et al. | |
| 10,610,664 B2 | | 4/2020 | Erbey, II et al. | |
| 10,617,843 B2 | | 4/2020 | Paz | |
| 10,631,788 B2 | | 4/2020 | Brody | |
| 10,639,451 B2 | | 5/2020 | Kearns et al. | |
| 10,639,452 B2 | | 5/2020 | Linares et al. | |
| 10,646,688 B2 | | 5/2020 | Hannon et al. | |
| 10,667,894 B2 | | 6/2020 | Forsell | |
| 10,668,249 B2 | | 6/2020 | Douglas et al. | |
| 10,675,134 B2 | | 6/2020 | Herrera et al. | |
| 10,675,435 B2 | | 6/2020 | Herrera et al. | |
| 10,682,214 B2 | | 6/2020 | Sufyan et al. | |
| 10,690,655 B2 | | 6/2020 | Duval | |
| 10,702,671 B2 | | 7/2020 | Terry | |
| 10,709,819 B2 | | 7/2020 | Littleton et al. | |
| D893,706 S | | 8/2020 | Lessmann | |
| 10,736,491 B2 | | 8/2020 | Truckai | |
| 10,737,057 B1 | | 8/2020 | Mikhail et al. | |
| 10,744,298 B1 | | 8/2020 | Bello et al. | |
| 10,751,493 B2 | | 8/2020 | Gregory et al. | |
| 10,758,704 B2 | | 9/2020 | Hickmott et al. | |
| 10,765,833 B2 | | 9/2020 | Kearns | |
| 10,765,834 B2 | | 9/2020 | Erbey, II et al. | |
| 10,772,755 B2 | | 9/2020 | Gregory | |
| 10,780,243 B2 | | 9/2020 | Reyes | |
| 10,780,244 B2 | | 9/2020 | Conway et al. | |
| 10,780,245 B2 | | 9/2020 | Schonfeldt | |
| 10,807,287 B2 | | 10/2020 | Rolsted et al. | |
| 10,814,097 B2 | | 10/2020 | Palmer | |
| 2002/0052624 A1 | * | 5/2002 | Bonutti | A61M 25/0662 606/198 |
| 2002/0077583 A1 | * | 6/2002 | Clemens | A61N 1/056 604/19 |
| 2002/0103472 A1 | * | 8/2002 | Kramer | A61M 25/0023 604/507 |
| 2003/0018293 A1 | | 1/2003 | Tanghoj et al. | |
| 2004/0039348 A1 | * | 2/2004 | Kim | A61M 3/0295 604/523 |
| 2004/0167478 A1 | * | 8/2004 | Mooney | A61M 25/0097 604/264 |
| 2005/0043715 A1 | | 2/2005 | Nestenborg et al. | |
| 2006/0118123 A1 | * | 6/2006 | Quinn | A61M 16/208 128/207.15 |
| 2006/0163097 A1 | | 7/2006 | Murray et al. | |
| 2006/0195135 A1 | * | 8/2006 | Ayoub | A61M 25/10 606/192 |
| 2006/0235458 A1 | * | 10/2006 | Belson | A61B 1/00135 606/191 |
| 2007/0021774 A1 | * | 1/2007 | Hogendijk | A61M 25/104 606/200 |
| 2008/0097350 A1 | * | 4/2008 | Bell | A61M 25/0032 604/266 |
| 2008/0188802 A1 | * | 8/2008 | Shah | A61M 25/1036 604/523 |
| 2008/0205481 A1 | * | 8/2008 | Faries | G01K 1/146 374/138 |
| 2009/0137985 A1 | | 5/2009 | Tanghoej et al. | |
| 2010/0094173 A1 | * | 4/2010 | Denton | A61M 1/7415 604/323 |
| 2010/0324535 A1 | | 12/2010 | Triel | |
| 2011/0190736 A1 | | 8/2011 | Young et al. | |
| 2011/0224653 A1 | | 9/2011 | Torstensen | |
| 2013/0138135 A1 | | 5/2013 | Rosen et al. | |
| 2013/0161208 A1 | | 6/2013 | Gustavsson | |
| 2013/0161227 A1 | | 6/2013 | Gustavsson | |
| 2013/0261608 A1 | | 10/2013 | Tanghoj | |
| 2014/0066905 A1 | | 3/2014 | Young | |
| 2014/0288517 A1 | | 9/2014 | Tsai et al. | |
| 2014/0336569 A1 | | 11/2014 | Gobel | |
| 2014/0378951 A1 | | 12/2014 | Dye | |

(56) References Cited

U.S. PATENT DOCUMENTS

| | | |
|---|---|---|
| 2015/0133898 A1 | 5/2015 | Murray et al. |
| 2015/0273180 A1 | 10/2015 | Schonfeldt |
| 2015/0273747 A1 | 10/2015 | Montes de Oca Balderas et al. |
| 2015/0290421 A1 | 10/2015 | Glickman et al. |
| 2015/0297862 A1 | 10/2015 | Sadik et al. |
| 2015/0320970 A1 | 11/2015 | Foley et al. |
| 2016/0067445 A1 | 3/2016 | Murray et al. |
| 2016/0184551 A1 | 6/2016 | Nyman et al. |
| 2016/0206469 A1 | 7/2016 | Prezelin |
| 2016/0287759 A1 | 10/2016 | Clarke et al. |
| 2016/0317715 A1 | 11/2016 | Rostami et al. |
| 2016/0325903 A1 | 11/2016 | Doerschner et al. |
| 2017/0000978 A1 | 1/2017 | Murray et al. |
| 2017/0021128 A1 | 1/2017 | Erbey, II et al. |
| 2017/0105826 A1 | 4/2017 | Erikstrup |
| 2017/0348137 A1 | 12/2017 | Hvid et al. |
| 2017/0348138 A1 | 12/2017 | Hvid et al. |
| 2018/0015250 A1 | 1/2018 | Tsukada et al. |
| 2018/0021481 A1 | 1/2018 | Yin et al. |
| 2018/0050173 A1 | 2/2018 | Kearns |
| 2018/0071482 A1 | 3/2018 | Fitzpatrick et al. |
| 2018/0369474 A1 | 12/2018 | Falleboe et al. |
| 2019/0099583 A1 | 4/2019 | Charlez et al. |
| 2019/0224402 A1 | 7/2019 | Henry et al. |
| 2019/0240060 A1 | 8/2019 | He et al. |
| 2019/0247549 A1 | 8/2019 | Nielsen |
| 2019/0314044 A1 | 10/2019 | Long et al. |
| 2019/0314188 A1 | 10/2019 | Barrientos |
| 2019/0314190 A1 | 10/2019 | Sanchez et al. |
| 2019/0321587 A1 | 10/2019 | McMenamin et al. |
| 2019/0321589 A1 | 10/2019 | Bonneau |
| 2019/0358075 A1 | 11/2019 | Scharich, III et al. |
| 2019/0358435 A1 | 11/2019 | Andersin et al. |
| 2019/0365561 A1 | 12/2019 | Newton et al. |
| 2019/0366038 A1 | 12/2019 | Denman et al. |
| 2019/0374324 A1 | 12/2019 | Luleci |
| 2019/0381291 A1 | 12/2019 | Feld |
| 2019/0388659 A1 | 12/2019 | Ruel |
| 2020/0001045 A1 | 1/2020 | McIntyre |
| 2020/0001049 A1 | 1/2020 | House |
| 2020/0016380 A1 | 1/2020 | Murray et al. |
| 2020/0022636 A1 | 1/2020 | Suehara et al. |
| 2020/0030135 A1 | 1/2020 | Woodyard |
| 2020/0030582 A1 | 1/2020 | Dong |
| 2020/0030595 A1 | 1/2020 | Boukidjian et al. |
| 2020/0037832 A1 | 2/2020 | Wang et al. |
| 2020/0054800 A1 | 2/2020 | Wilbourn et al. |
| 2020/0094017 A1 | 3/2020 | Erbey, II et al. |
| 2020/0101280 A1 | 4/2020 | Peddicord |
| 2020/0129731 A1 | 4/2020 | Brar et al. |
| 2020/0139109 A1 | 5/2020 | Imran |
| 2020/0146799 A1 | 5/2020 | Connors et al. |
| 2020/0146871 A1 | 5/2020 | Palmer |
| 2020/0163543 A1 | 5/2020 | Schutt et al. |
| 2020/0163699 A1 | 5/2020 | Bacich et al. |
| 2020/0179644 A1 | 6/2020 | Guldbaek |
| 2020/0179665 A1 | 6/2020 | Orr et al. |
| 2020/0188631 A1 | 6/2020 | Hannon et al. |
| 2020/0206389 A1 | 7/2020 | Vange |
| 2020/0206411 A1 | 7/2020 | Henry et al. |
| 2020/0206468 A1 | 7/2020 | Olson et al. |
| 2020/0206470 A1 | 7/2020 | Orr et al. |
| 2020/0214820 A1 | 7/2020 | Bunch et al. |
| 2020/0215303 A1 | 7/2020 | Erbey, II et al. |
| 2020/0222188 A1 | 7/2020 | Smith et al. |
| 2020/0222220 A1 | 7/2020 | Kappus et al. |
| 2020/0222659 A1 | 7/2020 | Schertiger et al. |
| 2020/0222660 A1 | 7/2020 | Erbey, II et al. |
| 2020/0222674 A1 | 7/2020 | Inoue et al. |
| 2020/0229964 A1 | 7/2020 | Staali et al. |
| 2020/0230349 A1 | 7/2020 | McMenamin et al. |
| 2020/0230356 A1 | 7/2020 | Utas et al. |
| 2020/0230382 A1 | 7/2020 | Siebert |
| 2020/0238048 A1 | 7/2020 | Palmer |
| 2020/0246587 A1 | 8/2020 | Tal et al. |
| 2020/0246589 A1 | 8/2020 | Starr |
| 2020/0246594 A1 | 8/2020 | Miller |
| 2020/0254215 A1 | 8/2020 | Portela et al. |
| 2020/0261692 A1 | 8/2020 | Palmer |
| 2020/0262868 A1 | 8/2020 | Ricca et al. |
| 2020/0268947 A1 | 8/2020 | Erbey, II et al. |
| 2020/0276046 A1 | 9/2020 | Staali et al. |
| 2020/0276410 A1 | 9/2020 | Son |
| 2020/0281760 A1 | 9/2020 | Fleming |
| 2020/0282092 A1 | 9/2020 | Paul et al. |
| 2020/0306502 A1 | 10/2020 | Luning et al. |
| 2020/0315445 A1 | 10/2020 | Cheng et al. |
| 2020/0324006 A1 | 10/2020 | Paul et al. |
| 2020/0330724 A1 | 10/2020 | Mikhail et al. |

FOREIGN PATENT DOCUMENTS

| | | |
|---|---|---|
| EP | 3315159 A1 | 5/2018 |
| EP | 3351208 A1 | 7/2018 |
| WO | 2009048375 A1 | 4/2009 |
| WO | 2018134591 A1 | 7/2018 |
| WO | 2018143487 A1 | 8/2018 |
| WO | 2019014344 A1 | 1/2019 |
| WO | 2019038732 A1 | 2/2019 |
| WO | 2019038734 A1 | 2/2019 |
| WO | 2019106581 A2 | 6/2019 |
| WO | 2019123004 A1 | 6/2019 |
| WO | 2019184222 A1 | 10/2019 |
| WO | 2019222644 A1 | 11/2019 |
| WO | 2019229597 A1 | 12/2019 |
| WO | 2020015804 A1 | 1/2020 |
| WO | 2020093698 A1 | 5/2020 |
| WO | 2020110046 A1 | 6/2020 |
| WO | 2020110051 A1 | 6/2020 |
| WO | 2020132731 A1 | 7/2020 |
| WO | 2020136503 A1 | 7/2020 |
| WO | 2020136645 A1 | 7/2020 |
| WO | 2020144302 A1 | 7/2020 |
| WO | 2020160738 A1 | 8/2020 |
| WO | 2020173531 A1 | 9/2020 |
| WO | 2020173942 A1 | 9/2020 |
| WO | 2020178711 A1 | 9/2020 |
| WO | 2020214944 A1 | 10/2020 |

* cited by examiner

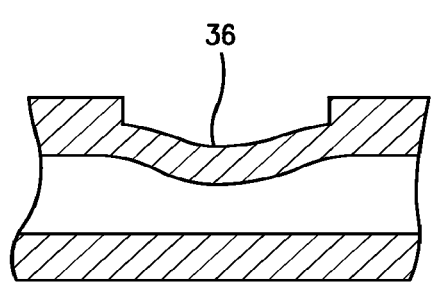
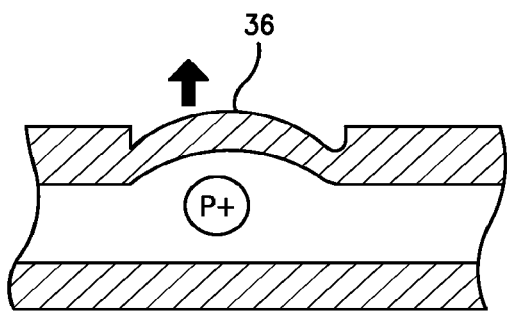
FIG. 4(a)  FIG. 4(b)
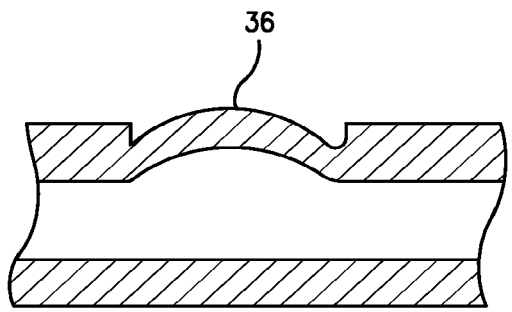
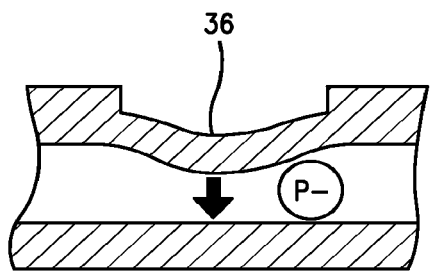
FIG. 5(a)  FIG. 5(b)

RECTAL DRAIN APPLIANCE

CROSS-REFERENCE

This application is a divisional of U.S. patent application Ser. No. 15/224,278, filed Jul. 29, 2016, which is a continuation of application of U.S. patent application Ser. No. 12/990,229, filed on Oct. 29, 2010, which is a U.S. National Phase of PCT/US09/42544, filed May 1, 2009, which claims the benefit of U.S. Provisional Application No. 61/049,578, filed on May 1, 2008, each of which is entirely incorporated herein by reference.

FIELD OF THE INVENTION

The present invention relates to a rectal appliance in the form of a drain tube having an inflatable balloon insertable into the rectum in use. Another aspect of the invention relates to a pressure level indicator for indicating the pressure level within the inflatable balloon(s) of a rectal or intestinal drain.

BACKGROUND TO THE INVENTION

U.S. Patent Publication Nos. 2005/054996 and 2005/137526 describe fecal management appliances in the form of elongate tubular elements. Each tubular element includes an inflatable balloon at the distal end, for anchoring the distal end in an operative position in the wearer's rectum. The tubular element includes a main drain passage, and two small-size auxiliary lumens, similar to each other and integrated into the wall of the drain passage. One of the lumens communicates with the balloon for passing inflation fluid between the balloon and an inflation port during inflation and deflation. The other of the lumens has an open end for injecting irrigation fluid from an irrigation port directly into the rectal cavity. The tubular element is collapsible in diameter, to facilitate passage through the anal sphincter. US-A-2005/054996 in particular emphasizes the significance of controlling carefully the inflation pressure in the balloon, to provide good anchoring in the rectum, while still ensuring normal blood perfusion in the soft tissue contacted by the balloon, and avoiding pressure necrosis of the soft tissue. In one form, pressure level indicators are used on the inflation lumen to provide a clinician with important indication of pressure. The pressure level indicators include a separate pressure sensor coupled to the inflation lumen near the inflation port, or a pressure indicator integrated in an inflation syringe, or spring loading the inflation syringe to act as a pressure stabilizer and indicator. The point at which a desired inflation pressure is reached, with respect to the volume of inflation fluid used, is also an important characteristic used by the clinician to assess whether the balloon is a correct size for a rectal cavity of the wearer. If an inflation pressure threshold is reached too quickly, this indicates that the balloon is too large; if an inflation pressure is never reached, this indicates that the balloon is too small.

Although not described explicitly in the above published applications, there are also several constraints affecting the size of the auxiliary lumens in the designs illustrated in these applications. Whereas the main tubular element is intended to be collapsible in diameter to facilitate passage through the anal sphincter, the auxiliary lumens have a small non-collapsing form to permit application of suction for forcibly withdrawing inflation fluid from the balloon when it is desired to deflate the balloon down to a minimum size. The non-collapsing nature of the lumens means that the lumens obstruct collapsing of the main tubular element. The auxiliary lumens are relatively small to minimize this obstructing effect, and enable the main tubular element to collapse to a desirably small form.

U.S. Patent Publication No. 2008/0312614 describes an ileostomy set used for drainage and collection of fluid/feces from the small intestine. This set includes a balloon catheter equipped with two balloons, a fixation balloon which is inflated in the large intestine and a blocking balloon which is inflated in the small intestine behind the Bauhin valve. Each of the balloons fills the entire lumen in which it is placed. The point at which a desired inflation pressure is reached in each of the balloons, with respect to the volume of inflation fluid used, is an important characteristic to assess whether each balloon is a correct size for the large and small intestine of the patient.

It would be desirable to further enhance the versatility and ease of use of such rectal drain appliances.

SUMMARY OF THE INVENTION

One aspect of the invention provides a pressure level indicator for the inflatable balloon(s) of a rectal drainage catheter or an intestinal drain. The pressure level indicator includes a mechanical element that flips between first and second distinct physical states depending on sensed pressure. The states may be different shapes of the element. The mechanical element may have a three-dimensional shape, such as a dome shape, that flips between a non-inverted state, and an inverted state. In one state, the dome projects like a popped-up button; in the other state, the dome is depressed like a valley or well. The mechanical element may form an integrally molded part of a plastics housing. The provision of a mechanical element that flips its state can provide an instantly recognizable and unambiguous indication of a certain pressure state, and can also be easier and quicker for a clinician to assess than having to read off a measurement value from a variable scale of a pressure sensor. The mechanical element may also be more compact, and/or more lightweight, and/or less expensive to provide, than a conventional variable pressure sensor. The pressure level indicator of this aspect of the invention may be integrated as part of a disposable appliance, without any significant increase in cost. For example, the pressure level indicator may be integrated into an inflation port housing of the appliance.

The mechanical element may flip from the first state to the second state when the sensed pressure crosses (exceeds or drops below) a threshold with respect to external pressure acting on the element. The mechanical element may be configured to flip back to the first state should the sensed pressure re-cross the threshold in the opposite direction, so that the element always provides an indication of the current pressure state. Alternatively, the mechanical element may remain permanently in the second state to provide a permanent record that the pressure threshold was crossed.

Multiple mechanical elements may be provided that flip at different pressure thresholds. For example, two mechanical elements may be provided to show whether the inflation pressure is in a desired inflation range. Additionally, or alternatively, a first mechanical element may indicate that a desired inflation pressure has been attained for achieving desired anchoring of the appliance in the rectum, and a second mechanical element may indicate that a desired deflation pressure has been attained for allowing easy and safe removal of the appliance from the rectum.

Another aspect of the invention provides a rectal drainage appliance comprising an inflatable balloon for insertion into the rectum. The appliance comprises first and second auxiliary lumens communicating with the inflatable balloon. The first auxiliary lumen is used as an inflation lumen. The second auxiliary lumen is used as a pressure sensing lumen for providing a direct indication of inflation pressure in the balloon, independent of dynamic pressure drop in the inflation lumen.

This aspect of the invention arises from an appreciation that a small sized inflation lumen can impose a resistance to flow of inflation fluid, and create a dynamic pressure drop while there is a flow of inflation fluid into the balloon during inflation, or out of the balloon during deflation. The dynamic pressure drop means that a measurement of pressure at the inflation port might not be an accurate indication of pressure in the balloon at all times. The provision of a second auxiliary lumen provides direct sensing of the internal pressure in the balloon, and enables a clinician to have an accurate indication of this internal pressure unaffected by any dynamic pressure drop in the inflation lumen.

In a preferred form, at least the second lumen is prefilled with inflation fluid. This minimizes the pressure drop between the balloon and the mechanical element as the second lumen fills with inflation fluid.

Another aspect of the present invention provides a tubular element of a rectal drain appliance, the tubular element having a main drain passage, at least one non-collapsing (or non-collapsible) auxiliary lumen, and at least one collapsing (or collapsible) auxiliary lumen. The collapsing auxiliary lumen preferably has a larger cross-sectional area than the non-collapsing auxiliary lumen, at least when the collapsing auxiliary lumen is in a distended shape. The non-collapsing auxiliary lumen may communicate with an inflatable balloon provided at a distal end of the tubular element. The collapsing auxiliary lumen may communicate directly or indirectly with an open space at the distal end of the tubular element.

This aspect of the invention arises from an appreciation that, although an auxiliary lumen associated with an inflatable balloon is beneficially non-collapsing to allow the application of suction, there is less constraint for an auxiliary lumen for irrigation. The third aspect of the invention enables a relatively large auxiliary lumen for injecting irrigation fluid. As well as making irrigation easier, the lumen may also be used in more versatile ways, for example, allowing the insertion of a temperature sensor or other medical device into the rectal cavity, without interfering substantially with drainage. When the supply of irrigation fluid, or the medical device, is removed from that lumen, the lumen can collapse to a small size, so that the provision of the large auxiliary lumen does not obstruct the desired collapsing property of the tubular element.

Viewed in another aspect, the invention provides a rectal drainage appliance comprising a tubular element having an inflatable balloon at a distal end for anchoring the appliance in the rectum. The appliance includes one or more of: (i) first and second auxiliary lumens communicating with the inflatable balloon to provide independent inflation and pressure monitoring paths coupled to the balloon; (ii) a pressure state indicator defined by a mechanical element configured to flip between first and second states or shapes responsive to sensed pressure; and (iii) a collapsible auxiliary lumen larger than the inflation lumen, and configured to permit admission of irrigation fluid or a medical device via the collapsible lumen to the distal end of the appliance.

An additional aspect of the invention is a pressure indicator or inflation port configured to act as an inflation fluid admission and withdrawal point for controlling the inflation state for each of the inflatable balloons of an intestinal drain of the type shown in U.S. Patent Publication No. 2008/0312614.

The above aspects may be used in combination, or any two of the above aspects may be selectively combined together, or any aspect may be used independently of the others. While features believed to be of importance have been emphasized above and in the following claims and description, the Applicant may seek to claim protection for any novel feature of idea disclosed herein and/or illustrated in the drawings whether or not emphasis has been placed thereon.

BRIEF DESCRIPTION OF THE DRAWINGS

FIG. 4(a) is a schematic sectional view illustrating a first configuration of molded mechanical element for the pressure indicator/inflation port.

FIG. 4(b) illustrates a flipped state of the first configuration of molded mechanical element for the pressure indicator/inflation port.

FIG. 5(a) is a schematic sectional view illustrating a second configuration of molded mechanical element for the pressure indicator/inflation port.

FIG. 5(b) illustrates a flipped state of the second configuration of molded element for the pressure indicator/inflation port.

DETAILED DESCRIPTION OF PREFERED EMBODIMENTS

Figure 1:
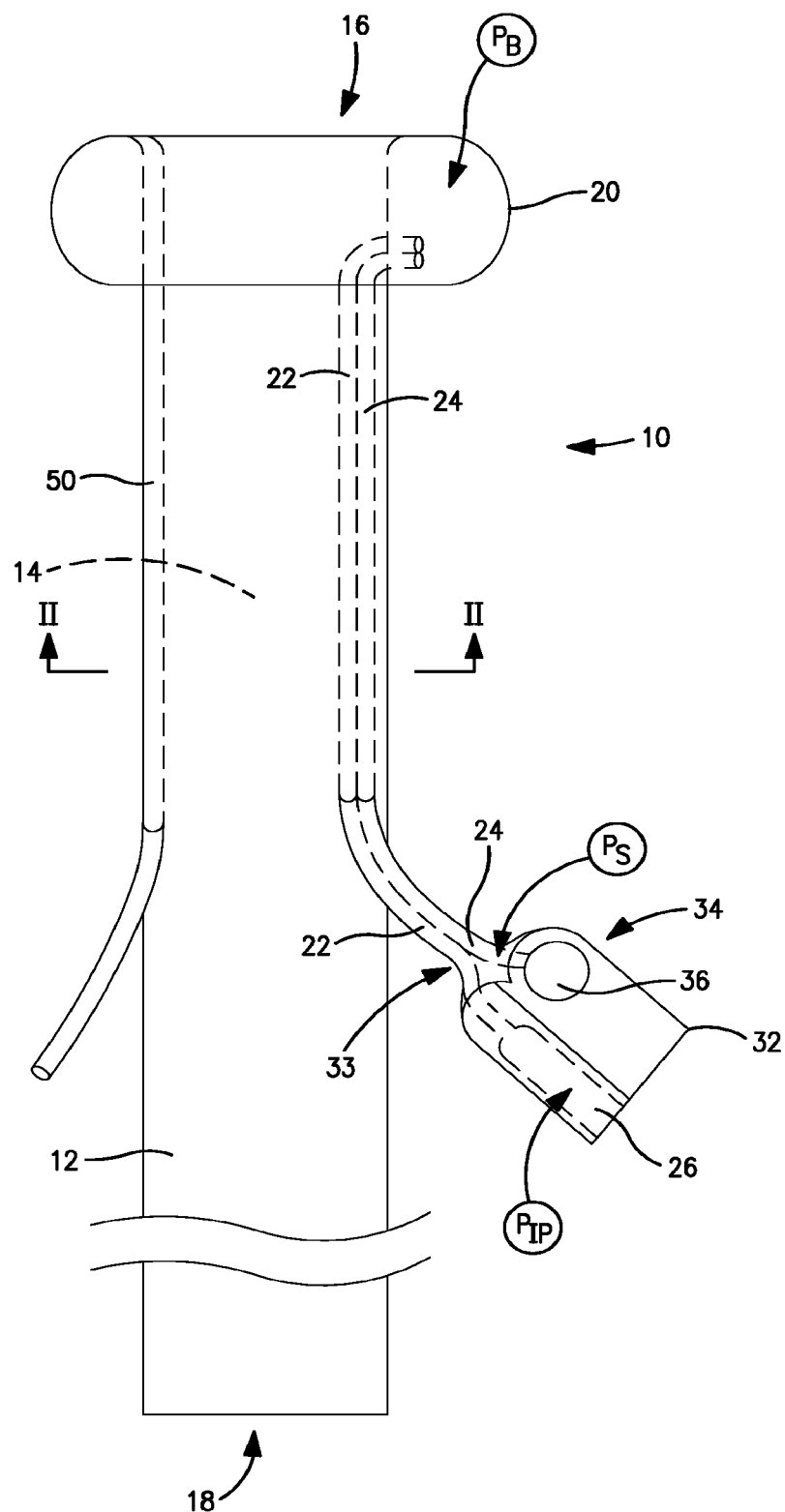
FIG. 1 is a schematic sectional view showing a first embodiment of a rectal drainage appliance.

The same reference numerals denote similar or equivalent features in each embodiment. Additional constructional details for rectal drainage tubes may be found in the aforementioned U.S. Patent Publication Nos. 2005/054996 and 2005/137526, the contents of which are incorporated herein by reference.

Figure 2:
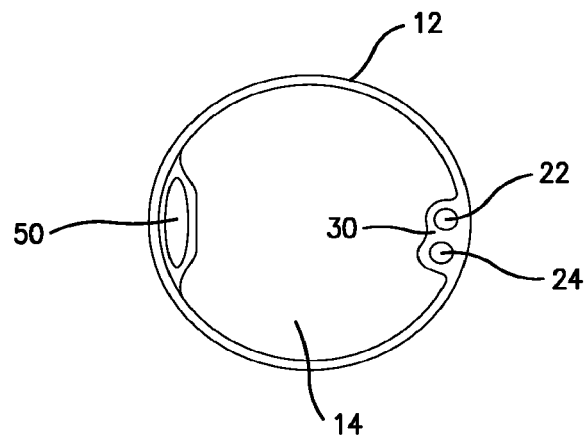
FIG. 2 is a schematic cross-sectional view along the line II-II of FIG. 1.

Referring to FIGS. 1 and 2, a rectal drainage appliance 10 generally comprises a flexible elongate tubular element 12 defining a drain channel 14 for passage of stool. The element 12 has a distal end 16 for insertion through the anus into the rectum of a wearer, and a proximal end 18 for coupling to a fecal collector (not shown) such as a pouch. Typically, element 12 is about 1.5 m long, and has an outer diameter of about 23 mm. The element 12 can collapse down to about 8 mm in diameter to facilitate passage through the anal sphincter. The element 12 is typically made of soft plastics, such as silicone. The element 12 may be provided with an additional odor barrier layer, or a separate odor barrier sleeve (not shown), to obstruct transpiration of malodors through the wall of the drain channel 14.

An inflatable balloon 20 is provided at the distal end 16, for anchoring the distal end 16 inside the rectum. The inflatable balloon 20 is generally cuff or toroid shaped, and extends around the distal end 16. The inflatable balloon 20 may be configured of material that stretches elastically as the balloon 20 inflates, but it is preferred that the balloon 20 be pre-formed in an inflated shape. Such pre-forming enables the inflation pressure to be reduced in use, because there is little or no elastic return force in the balloon wall acting against desired inflation.

The tubular element 12 comprises first and second auxiliary lumens 22, 24 that both communicate with the balloon 20. The lumens 22, 24 may be of about the same size (e.g., cross-section area) or the second lumen 24 may be smaller than the first lumen 22. One of the lumens 22, 24, for example the first lumen 22, is used as an inflation lumen for passing inflation fluid between the balloon 20 and an inflation port 26, for inflating or deflating the balloon 20 when desired. The other lumen, for example the second lumen 24, is used as a pressure sense lumen for providing a direct indication of pressure inside the balloon 20, independent of any dynamic pressure drop in the inflation lumen 22, as explained below.

The first and second auxiliary lumens 22, 24 are configured to be substantially non-collapsing in use, in order to allow the application of suction for forcibly withdrawing inflation fluid and deflating the balloon 20 completely down to a minimum size. This applies for both elastic and pre-formed types of balloon, but is especially important for the pre-formed type because there is no elastic return force in the balloon wall tending to act to expel inflation fluid. In order to avoid the non-collapsing auxiliary lumens 22, 24 from compromising desired collapsing of the element 12 overall, the first and second lumens 22, 24 are relatively small in size (e.g., a diameter of about 2 mm or less). Such a small diameter size can impose a resistance to substantial volume flow of inflation fluid in the lumen 22, 24, thereby causing a dynamic pressure drop in the inflation lumen 22 during inflation or deflation of the balloon 20. The dynamic pressure drop creates a difference between the fluid pressure $P_B$ within the balloon 20, and the fluid pressure $P_{IP}$ seen at the inflation port end of the inflation lumen 22. This can make pressure measurements taken from the inflation lumen 22 inaccurate, or at least ambiguous, during inflation or deflation until fluid flow has stopped. However, the provision of an additional pressure sense lumen 24 in the present embodiment enables direct sensing of fluid pressure $P_B$ within the balloon 20, using a path that is significantly less affected by dynamic pressure drop resulting from volume flow in the inflation lumen 22. Since the pressure sensing apparatus will generally not itself cause significant volume flow, the sensed pressure $P_S$ at the proximal end of the sensing lumen 24 is a much more accurate, stable, unambiguous and continuous representation of the fluid pressure $P_B$ within the balloon 20 throughout inflation and deflation processes. Moreover, since the both auxiliary lumens 22, 24 have non-collapsing walls, the auxiliary lumen 24 also allows accurate sensing of low pressure in the balloon 20 as a result of application of suction to deflate the balloon 20. This enables a clinician to observe the inflation pressure reliably, and also the point at which the inflation pressures reaches a certain level for assessing whether the balloon size is in fact suitable for the wearer. At least the second auxiliary lumen 24 may be pre-filled with inflation fluid to allow immediate use, without requiring any air to be expelled, or additional filling of inflation fluid to ready appliance before use.

In the present embodiment, the first and second auxiliary lumens 22, 24 are grouped together into a common extrusion 30. The extrusion 30 has a generally figure-of-8, or "B" shape. The first and second auxiliary lumens 22, 24 may be independent lumens within, or outside, the tubular element 12, but in the preferred form at least one (and preferably both) of the lumens 22, 24 are attached to, or integrally molded with, the tubular element 12 along a significant portion of the auxiliary lumen length.

Also in the present embodiment, the sensing lumen 24 leads to the same housing 32 as that containing or carrying the inflation port 26. The housing 32 further comprises or carries first and second nodes 33 coupled to the auxiliary lumens 22, 24. In one form, the housing 32 may comprise or carry an additional pressure sensing port (not shown) for allowing connection of an external pressure sensor (not shown) for monitoring the sensed pressure via the sensing lumen 24. However, in the preferred form, the housing 32 includes an integral pressure indicator 34 responsive to the pressure sensed via the sensing lumen 24.

Figure 3:
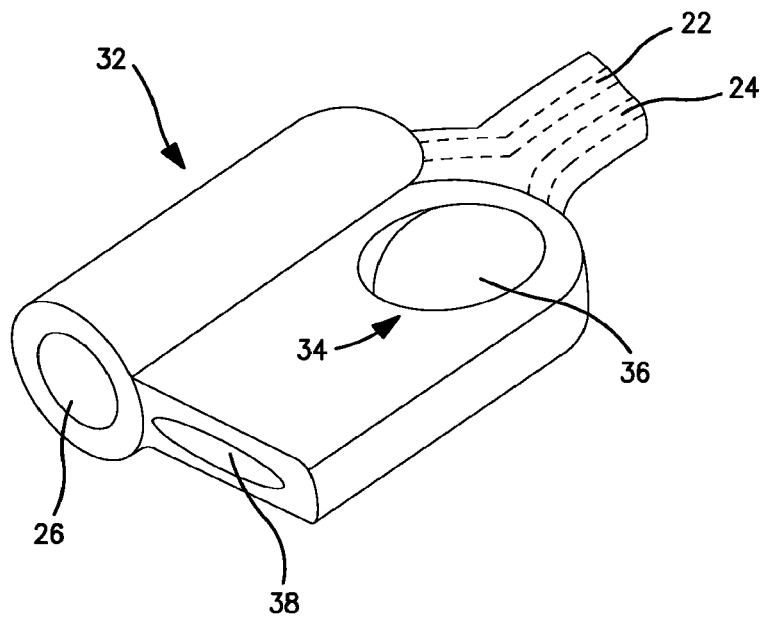
FIG. 3 is a schematic perspective view showing in isolation the pressure indicator or inflation port of the first embodiment or an intestinal drain including an integrated pressure sensor.

Referring to FIGS. 3-5, the pressure (or pressure state) indicator 34 comprises a mechanical element 36 that flips between first and second distinct physical states (e.g., shapes) depending on the sensed pressure. In the illustrated form, the mechanical element 36 has an inverting three-dimensional shape, such as a dome shape, the inverted or non-inverted state of which indicates the pressure level state. In one state, the dome projects like a popped-up button; in the other state, the dome is depressed like a valley or well. The mechanical element 36 is an integrally molded part of the housing 32. The mechanical element 36 may flip from the first state to the second state when the sensed pressure crosses (exceeds or drops below) a pressure threshold with respect to external pressure acting on the element. FIG. 4(a) shows a first configuration of mechanical element 36 molded in a first depressed state, and FIG. 4b shows the mechanical element 36 of the first configuration flipping to a second projecting state when the pressure P+ behind the element 36 exceeds ambient external pressure by a certain threshold. FIG. 5(a) shows an alternative second configuration of mechanical element 36 molded in a first projecting state, and FIG. 5(b) shows the mechanical element 36 of the second configuration flipping to a second depressed state when the pressure P− behind the element drops below ambient external pressure by a certain threshold.

The pressure (differential) at which the mechanical element 36 flips may be set by design of the material properties, the geometry of the three-dimensional shape, and the thickness and resilience of the element 36. Additionally, an auxiliary reinforcing member (not shown) may be used to reinforce the element 36 and provide additional control. The mechanical element 36 may be configured to flip back to the first state should the sensed pressure re-cross the threshold in the opposite direction, so that the element 36 always provides an indication of the current pressure state. Alternatively, the mechanical element 36 may be configured to remain permanently in the second state, thereby providing a permanent record that the pressure threshold was crossed.

As best seen in FIG. 3, during manufacture, the housing 32 is molded with an internal cavity with a temporary opening 38 on one side in which a mold core is received for molding the interior shape of the mechanical element 36. In order to complete the housing 32, the temporary opening 38 is later plugged or sealed closed (for example, by welding or adhesive).

The use of mechanical element 36 to indicate pressure by flipping between distinct states (e.g., shapes) can provide an instantly recognizable and unambiguous indication of a certain pressure state, and can also be easier and quicker for a clinician to assess than having to read off a measurement value from a variable scale of a pressure sensor. The mechanical element 36 may enable the pressure indicator 34 to be any of more compact, more lightweight, and/or less expensive than a conventional variable pressure sensor. The pressure indicator 34 is thus suitable to be included as an integral part of a disposable rectal drainage appliance 10. The pressure (or pressure state) indicator 34 having mechanical element 36 may also be used in an intestinal drainage or drain appliance device having an inflatable balloon, see, e.g., U.S. Patent Publication No. 2008/0312614.

Figure 6:
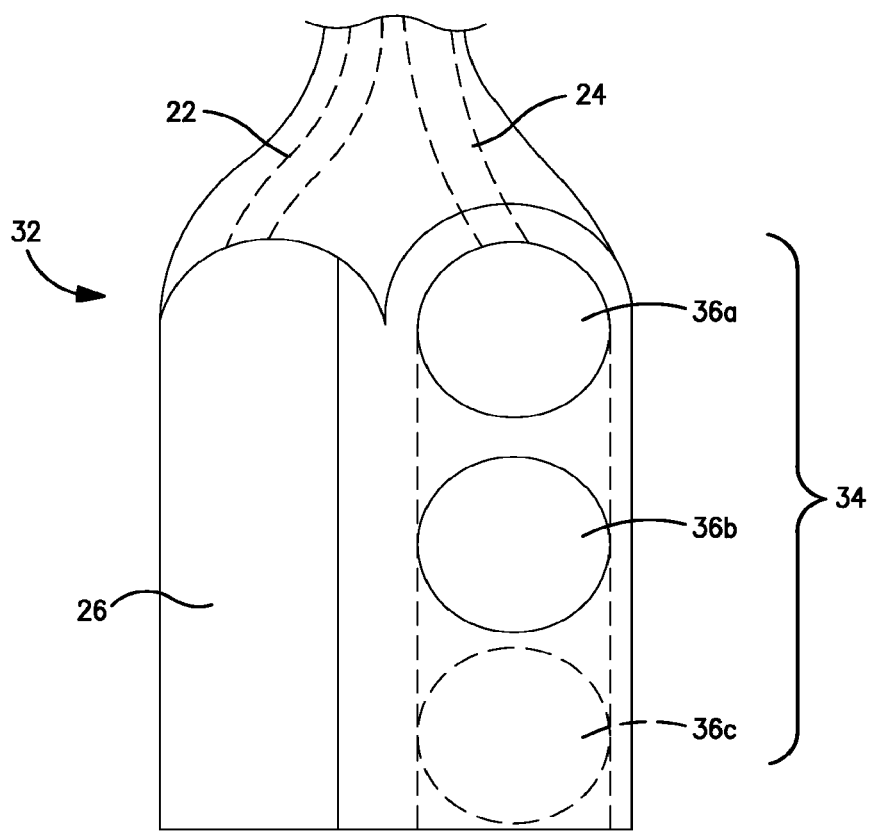
FIG. 6 is a schematic perspective view showing an alternative pressure indicator in a second embodiment of the pressure indicator/inflation port, including multiple state indicators.

In the embodiment of FIGS. 1-5, the pressure indicator 34 includes a single mechanical element 36 that is configured to represent a single pressure state, such as a predetermined inflation pressure level having been reached (using the first configuration of FIGS. 4(a) and 4(b)). The second embodiment illustrated in FIG. 6 provides two or more mechanical elements 36a, 36b, etc. each configured to indicate a respective different pressure state. For example, first and second mechanical elements 36a, 36b may be provided to show whether the inflation pressure is in a desired inflation range, the lower limit of which is indicated using one mechanical element 36a, and the upper level of which is indicated by the other mechanical element 36b. Both mechanical elements 36a and 36b may be of the first configuration (FIGS. 4(a) and 4(b)). This can enable the clinician to determine whether the inflation pressure is within an optimum operative range, even if the range is relatively narrow. Additionally, or alternatively, the first mechanical element 36a may indicate that a desired inflation pressure has been attained for achieving desired anchoring of the appliance in the rectum, and a further mechanical element (e.g., 36b or 36c) may indicate that a desired deflation or suction pressure has been attained in the balloon 20, ensuring that the balloon 20 is in its fully collapsed form allowing easy and safe removal of the appliance 10 from the rectum. This further element may be of the second configuration (FIGS. 5(a) and 5(b)).

Referring again to FIGS. 1 and 2, the tubular element 12 further comprises a collapsing auxiliary lumen 50. The collapsing lumen 50 has a cross-sectional area (when in a distended state indicated in phantom) larger than that of each of the first and second non-collapsing lumens 22, 24. In one form, the collapsing lumen 50 has a distended cross-sectional diameter of between about 2 mm and 5 mm. The collapsing lumen 50 communicates directly or indirectly with the opening at the distal end 16 of the tubular element 12. In use, the collapsing lumen 50 permits easy injection of irrigating fluid into the rectal cavity via the lumen 50. The large size of the lumen 50 allows easier flow of irrigation fluid at a lower pressure than does, for example, a relatively small size irrigation lumen used in the prior art. The large size of the lumen 50 also permits easy insertion of a medical device (for example, a temperature sensor) into the rectal cavity, which might not be possible, at least not as easily practicable, using the relatively small auxiliary lumen of the prior art. When the source of irrigation fluid, or the medical device, is removed, the lumen 50 can collapse down to its compact state. Either the wall of the lumen 50 is resilient to collapse the lumen 50 with a resilient return force to its compact state, or the wall of the lumen 50 is flexible to permit collapsing when the lumen 50 is compressed. Therefore, the provision of lumen 50 does not compromise the desired collapsing of the tubular element 12, nor does it obstruct substantially drainage of effluent via the drain channel 14 within the tubular element 12 when the lumen 50 is in its normal collapsed or compact state.

It will be appreciated that any of the ideas of (i) the collapsing lumen 50, (ii) the dual lumens 22, 24 communicating with the inflatable balloon 20, and (iii) the pressure indicator 34, may be used selectively in combination with, or independently of, any of the other ideas. However, greater synergy results as more of the ideas are combined.

Figure 7:
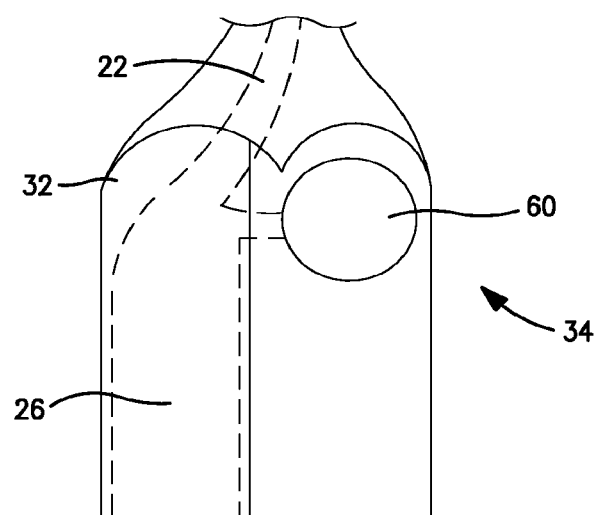
FIG. 7 is a schematic view of an alternative pressure indicator/inflation port in a third embodiment of the invention.

Referring to FIG. 7, a pressure indicator 60 is shown similar to the pressure indicator 34 described previously, except that the pressure indicator 60 does not communicate with a dedicated sense lumen, and instead is responsive to the inflation pressure in the inflation lumen 22. The pressure indicator 60 is integrated into the housing 32, and communicates directly with the port 26 and the lumen 22. This embodiment may be useful to implementing an alternative pressure indicator for existing designs of tubular element without a dedicated sense lumen independent of the inflation lumen 22, such as the appliances described in the aforementioned U.S. Patent Publication Nos. 2005/054996 and 2005/137526.

Figure 8:
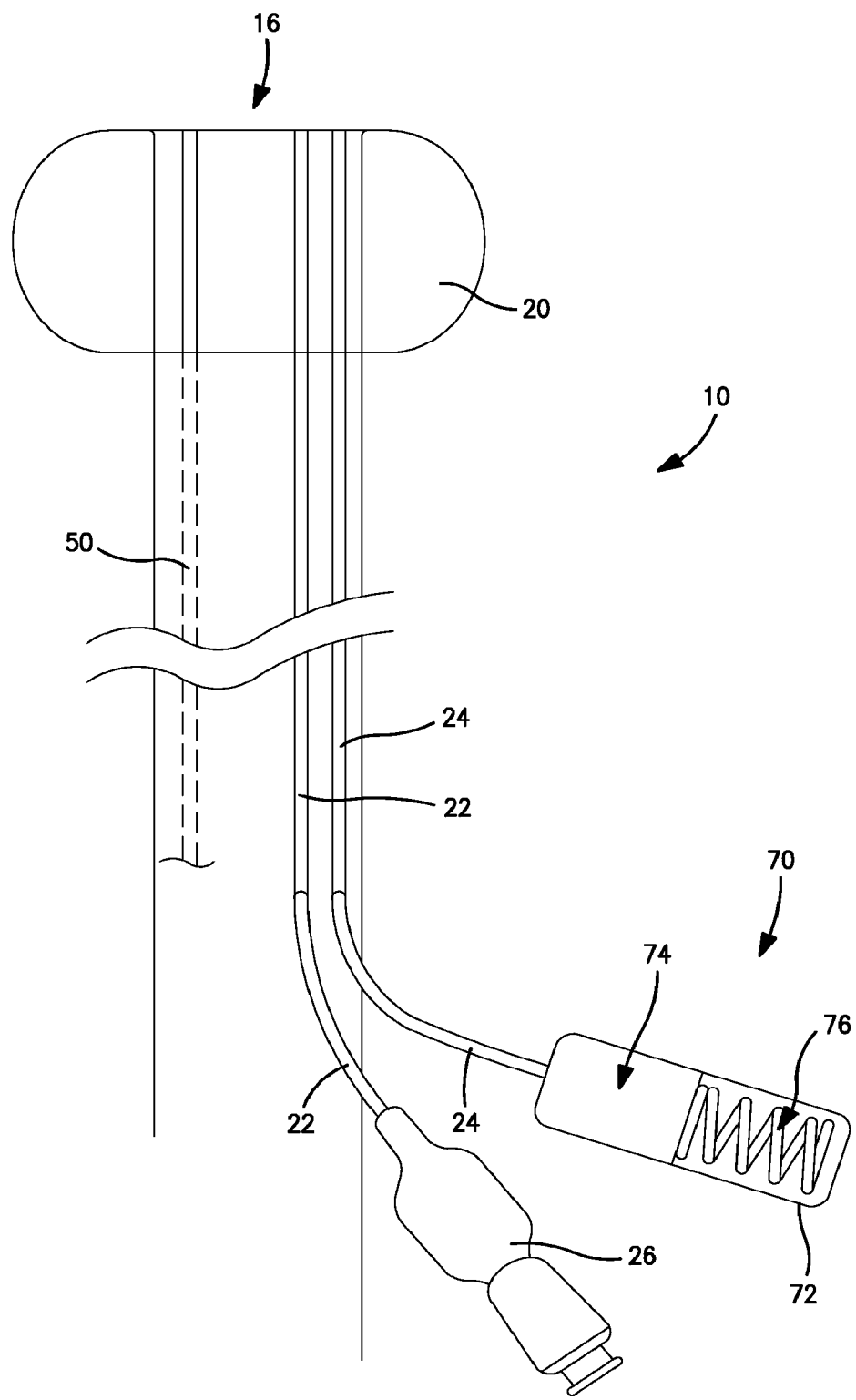
FIG. 8 is a schematic partial view of a fourth embodiment of a rectal drainage appliance.

Referring to FIG. 8, a fourth embodiment is illustrated implementing the collapsing auxiliary lumen 50 communicating with the distal end 16, and the dual non-collapsing lumens 22, 24 communicating with the balloon 20. An alternative pressure sensor 70 is provided coupled to the sense lumen 24. The pressure sensor 70 comprises a housing 72 containing a plunger 74 biased by a spring 76. At least a portion of the housing 72 is transparent to permit viewing of the position of the plunger 74, which position is directly indicative of the balloon pressure sensed via the sense lumen 24.

The foregoing description illustrates preferred embodiments of the invention. Many equivalents, modifications and improvements may be used without departing from the scope of the invention as claimed.

The invention claimed is:

1. A rectal drainage appliance comprising:
   a tubular element defining a drain passage for effluent from a rectum;
   an inflatable balloon at a first distal end of the tubular element for insertion into the rectum;
   a first auxiliary lumen communicating with the inflatable balloon, the first auxiliary lumen being substantially non-collapsing and having a first cross-section area; and
   a collapsing auxiliary lumen extending to the distal end of the tubular element, the collapsing auxiliary lumen having a second cross-section area that is (i) larger than the first cross section area when the collapsing auxiliary lumen is in a distended state, and (ii) not greater than the first cross-section area when the collapsing auxiliary lumen is in a collapsed state;
   wherein the collapsing auxiliary lumen extends, over at least a part of its length, within the tubular element.

2. The rectal drainage appliance of claim 1, wherein the collapsing auxiliary lumen is an irrigation lumen.

3. The rectal drainage appliance of claim 1, wherein the first auxiliary lumen and the collapsing auxiliary lumen are attached to, or integrally molded with, the tubular element.

4. The rectal drainage appliance of claim 1, wherein the first auxiliary lumen extends, over at least a part of its length, within the tubular element.

5. The rectal drainage appliance of claim 1, further comprising a second auxiliary lumen having a non-collapsing wall, and communicating with the inflatable balloon.

6. The rectal drainage appliance of claim 5, wherein the second auxiliary lumen is prefilled with inflation fluid.

7. The rectal drainage appliance of claim 5, wherein the first auxiliary lumen is up to three times larger in cross-sectional area than the second auxiliary lumen.

8. The rectal drainage appliance of claim 5, wherein the second auxiliary lumen has a diameter of about 2 mm or less.

9. The rectal drainage appliance of claim 5, wherein the second auxiliary lumen is attached to, or integrally molded with, the tubular element.

10. The rectal drainage appliance of claim 5, wherein the second auxiliary lumen communicates with the inflatable balloon at the distal end of the tubular element.

11. The rectal drainage appliance of claim 1, wherein the first auxiliary lumen is an inflation lumen.

12. The rectal drainage appliance of claim 1, wherein the first auxiliary lumen has a diameter of about 2 mm or less.

13. The rectal drainage appliance of claim 1, wherein the collapsing auxiliary lumen is releaseably connected to a thermometer.

14. The rectal drainage appliance of claim 1, wherein the collapsing auxiliary lumen has a cross-sectional diameter in the range of 2 mm and 5 mm when said collapsing auxiliary lumen is in the distended state.

15. The rectal drainage appliance of claim 1, further comprising a pressure indicator for sensing a balloon pressure coupled to the first auxiliary lumen for visually indicating, without having to read off a measurement value, a pressure level within the balloon while in use in the rectum.

16. The rectal drainage appliance of claim 15, wherein the pressure indicator comprises a visually accessible first mechanical element having a three dimensional shape configured to flip from a depressed physical shape to a projected physical shape when the balloon pressure reaches or crosses a predetermined level that exceeds ambient pressure.

17. A rectal drainage appliance, comprising:
a tubular element defining a drain passage for effluent from a rectum;
an inflatable balloon at a first distal end of the tubular element for insertion into the rectum;
a first auxiliary lumen communicating with the inflatable balloon, the first auxiliary lumen being substantially non-collapsing and having a first cross-section area;
a collapsing auxiliary lumen extending to the distal end of the tubular element, the collapsing auxiliary lumen having a second cross-section area that is (i) larger than the first cross section area when the collapsing auxiliary lumen is in a distended state, and (ii) not greater than the first cross-section area when the collapsing auxiliary lumen is in a collapsed state; and
a pressure indicator for sensing a balloon pressure coupled to the first auxiliary lumen for visually indicating, without having to read off a measurement value, a pressure level within the balloon while in use in the rectum;
wherein the pressure indicator comprises a visually accessible first mechanical element having a three dimensional shape configured to flip from a depressed physical shape to a projected physical shape when the balloon pressure reaches or crosses a predetermined level that exceeds ambient pressure; and
wherein the three-dimensional shape is an invertible dome.

18. A rectal drainage appliance comprising:
a tubular element defining a drain passage for effluent from a rectum;
an inflatable balloon at a first distal end of the tubular element for insertion into the rectum;
a first non-collapsing auxiliary lumen communicating with the inflatable balloon; and
a collapsible auxiliary lumen extending to the distal end of the tubular element, wherein at least a portion of the collapsible auxiliary lumen extends along the tubular element within the tubular element.

19. The rectal drainage appliance of claim 18, wherein the first auxiliary lumen has a first cross-sectional area; and
wherein the collapsing auxiliary lumen has a second cross-sectional area that is (i) larger than the first cross-sectional area when the collapsing auxiliary lumen is in a distended state, and (ii) not greater than the first cross-sectional area when the collapsing auxiliary lumen is in a collapsed state.

20. The rectal drainage appliance of claim 18, wherein the collapsible auxiliary lumen has an oblong cross-sectional shape.

* * * * *